(12) United States Patent
Ohashi et al.

(10) Patent No.: US 10,432,715 B2
(45) Date of Patent: Oct. 1, 2019

(54) ELECTRONIC APPARATUS, SYSTEM AND SYNCHRONIZATION METHOD

(71) Applicant: Toshiba Client Solutions CO., LTD., Koto-ku, Tokyo (JP)

(72) Inventors: Jun Ohashi, Ome Tokyo (JP); Akiyoshi Sougen, Ome Tokyo (JP)

(73) Assignee: Toshiba Client Solutions Co., LTD., Tokyo (JP)

( * ) Notice: Subject to any disclaimer, the term of this patent is extended or adjusted under 35 U.S.C. 154(b) by 479 days.

(21) Appl. No.: 14/677,048

(22) Filed: Apr. 2, 2015

(65) Prior Publication Data

US 2016/0072882 A1  Mar. 10, 2016

(30) Foreign Application Priority Data

Sep. 10, 2014  (JP) ................................ 2014-184264

(51) Int. Cl.
| | | |
|---|---|---|
| *H04L 29/08* | (2006.01) | |
| *G06F 19/00* | (2018.01) | |
| *A61B 5/00* | (2006.01) | |
| *H04W 4/80* | (2018.01) | |
| *A61B 5/11* | (2006.01) | |

(52) U.S. Cl.
CPC ........ *H04L 67/1095* (2013.01); *A61B 5/6802* (2013.01); *G06F 19/3418* (2013.01); *G06F 19/3481* (2013.01); *H04L 67/04* (2013.01); *H04L 67/12* (2013.01); *A61B 5/1123* (2013.01); *H04W 4/80* (2018.02)

(58) Field of Classification Search
CPC ..... H04L 67/1095; H04L 67/04; H04L 67/12; G06F 19/3418; G06F 19/3481; H04W 4/008; A61B 5/6802; A61B 5/1123
See application file for complete search history.

(56) References Cited

U.S. PATENT DOCUMENTS

| | | | |
|---|---|---|---|
| 6,493,743 B2 | 12/2002 | Suzuki | |
| 8,880,467 B1 * | 11/2014 | Muthusrinivasan | .. H04L 67/146 |
| | | | 707/632 |
| 9,774,564 B2 * | 9/2017 | Quan | ...................... H04L 67/06 |

(Continued)

FOREIGN PATENT DOCUMENTS

| | | |
|---|---|---|
| JP | 05-210507 A | 8/1993 |
| JP | 10-333967 A | 12/1998 |

(Continued)

*Primary Examiner* — Arvin Eskandarnia
*Assistant Examiner* — Chhian (Amy) Ling
(74) *Attorney, Agent, or Firm* — Knobbe, Martens, Olson & Bear, LLP

(57) ABSTRACT

According to one embodiment, an electronic apparatus includes a registration module, a transmission processor, and a reception processor. The registration module registers second data in a first file in a non-volatile storage device. The transmission processor transmits third data which is at least part of the first file to a server. The third data includes data registered in the first file after the data is previously transmitted to the server. The server includes a second file for registering all data transmitted from at least one second electronic apparatus, which corresponds to a user, including the electronic apparatus. The reception processor does not receive the fourth data from the server when only the electronic apparatus corresponds to the user.

18 Claims, 9 Drawing Sheets

(56) References Cited

U.S. PATENT DOCUMENTS

| | | | |
|---|---|---|---|
| 2002/0007391 A1 | 1/2002 | Suzuki | |
| 2012/0203491 A1 | 8/2012 | Sun et al. | |
| 2013/0073691 A1* | 3/2013 | Quan | H04L 67/06 709/219 |
| 2013/0285836 A1* | 10/2013 | Proud | H01F 38/14 340/870.02 |
| 2014/0236531 A1* | 8/2014 | Carter | A61B 5/1123 702/141 |
| 2015/0163210 A1* | 6/2015 | Meyers | H04W 4/70 726/4 |
| 2015/0228134 A1* | 8/2015 | Tehranchi | G07C 9/00111 340/5.61 |
| 2015/0350752 A1* | 12/2015 | Solomon | H04Q 9/04 340/870.01 |

FOREIGN PATENT DOCUMENTS

| | | |
|---|---|---|
| JP | 2000-222268 | 8/2000 |
| JP | 2014-032639 A | 2/2014 |
| JP | 2014-511189 | 5/2014 |
| JP | 2014-164566 | 9/2014 |

\* cited by examiner

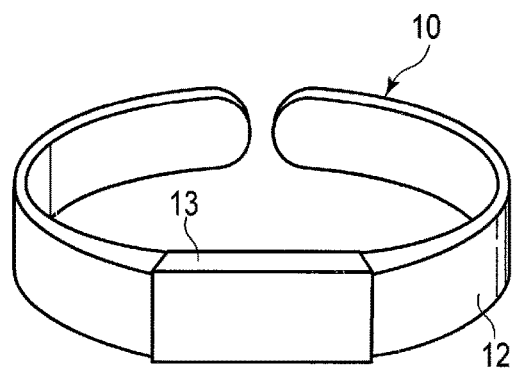
F I G. 1
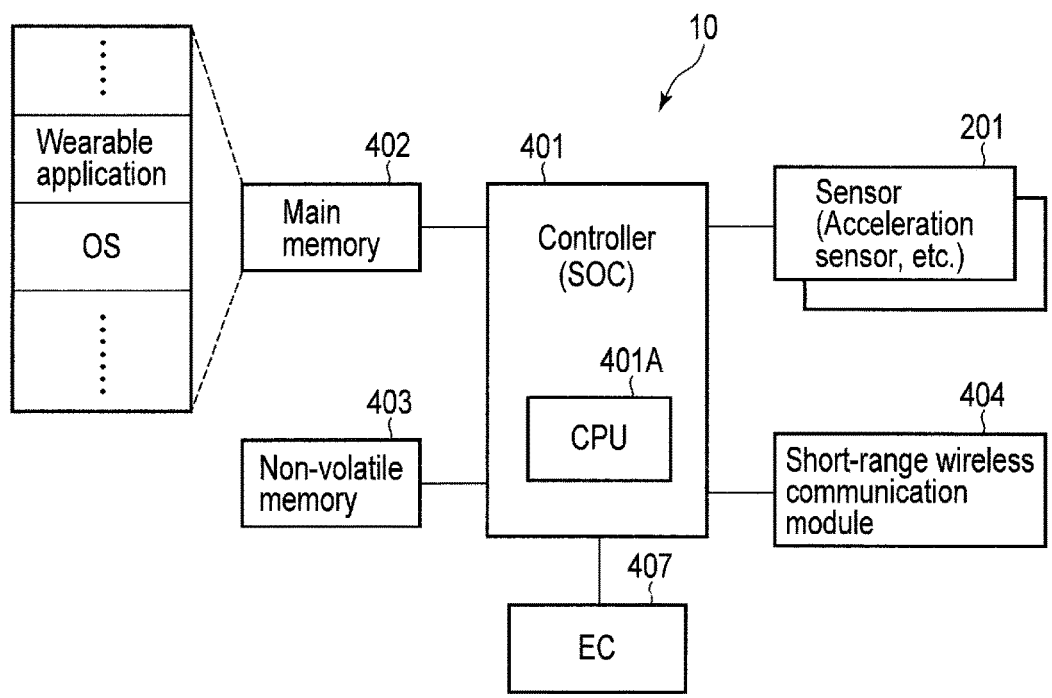
F I G. 2

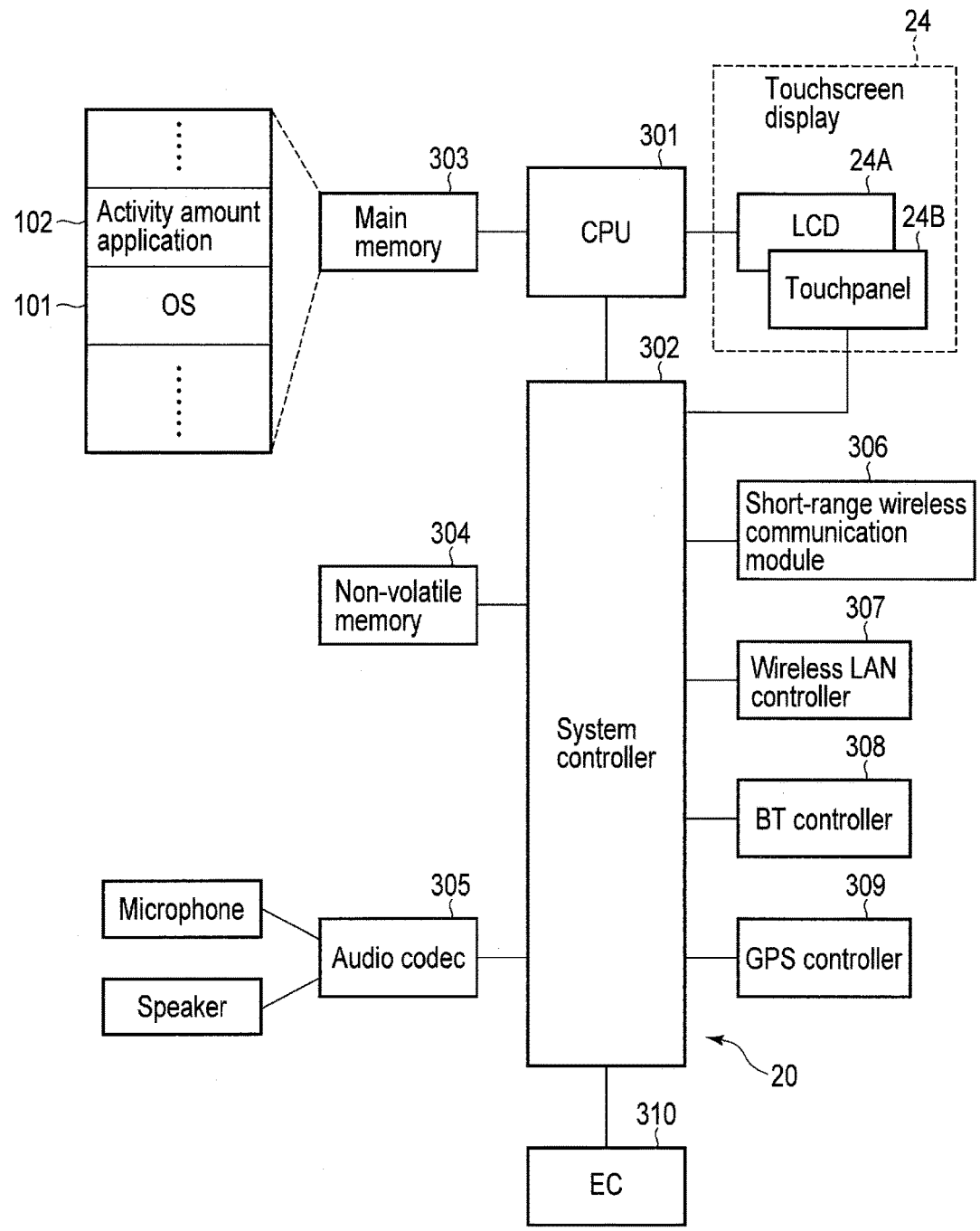
F I G. 3

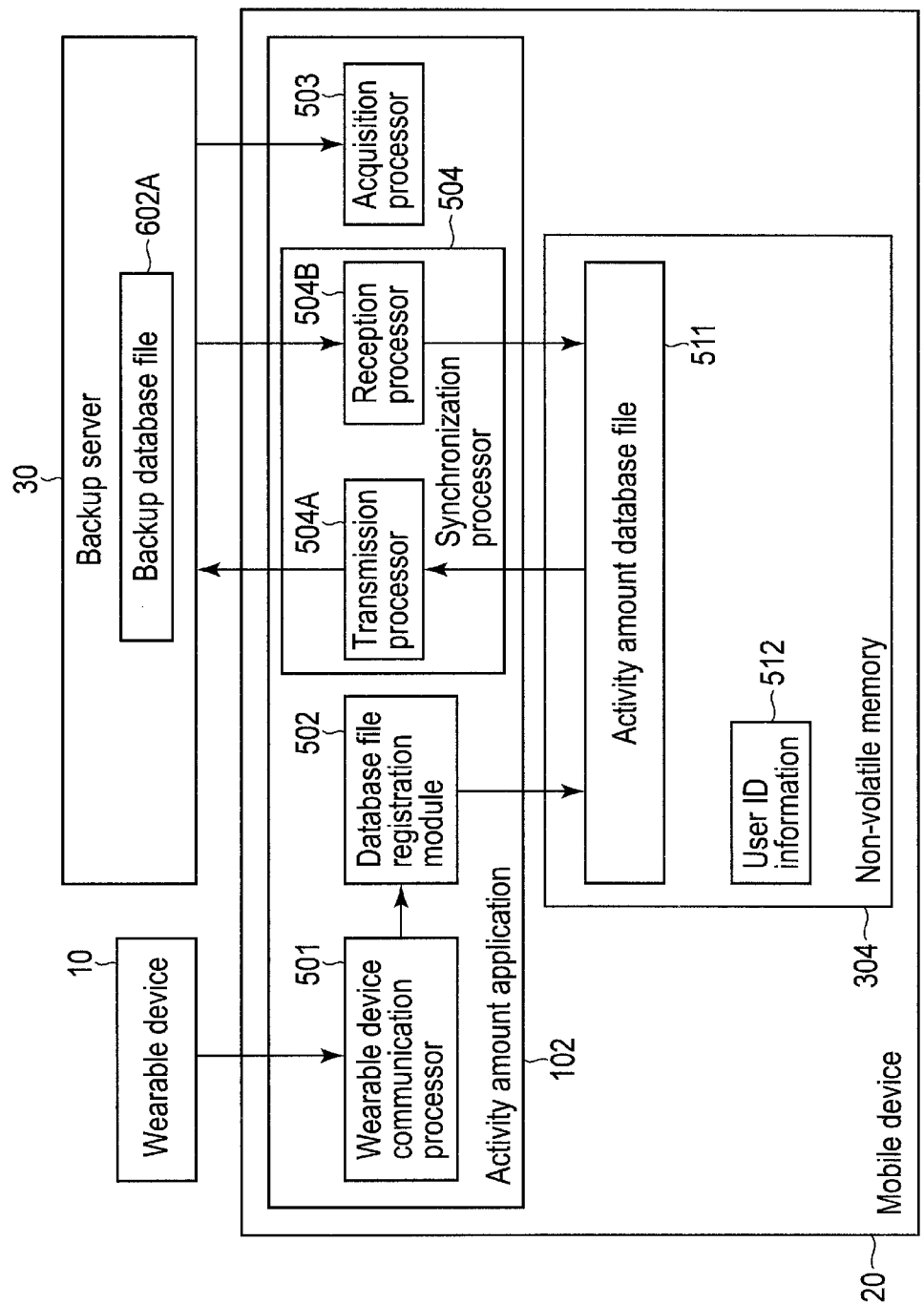
F I G. 4

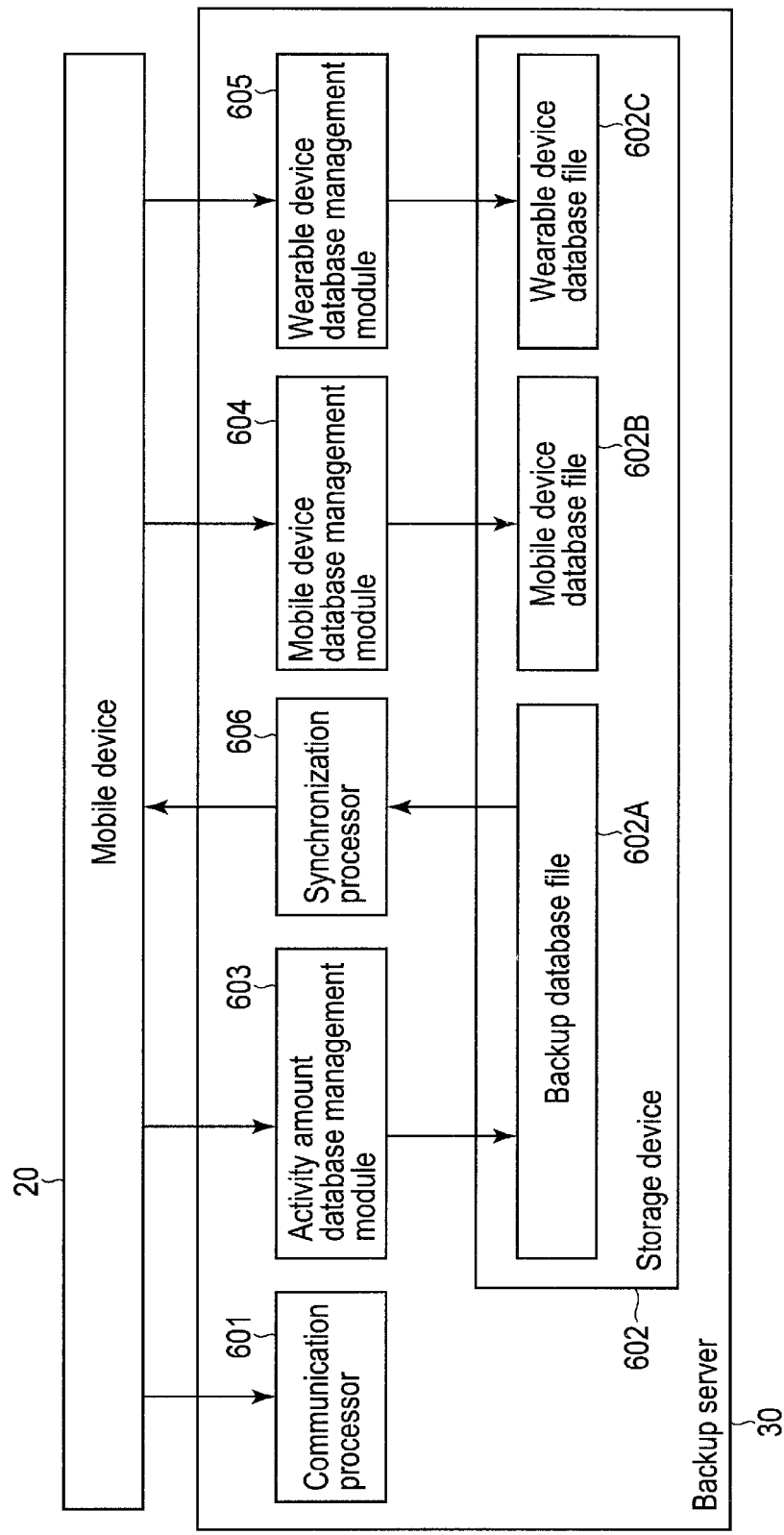
F I G. 5

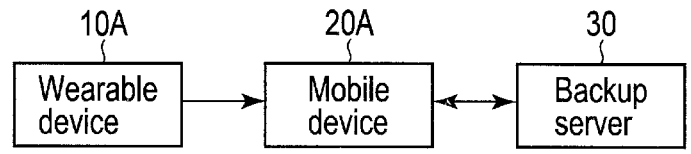
F I G. 6
| User ID | Mobile device ID | Last synchronization time information |
|---|---|---|
| User ID 1 | Mobile device ID 1 | Last synchronization time information 1 |
F I G. 7
| User ID | Wearable device ID |
|---|---|
| User ID 1 | Wearable device ID 1 |
F I G. 8

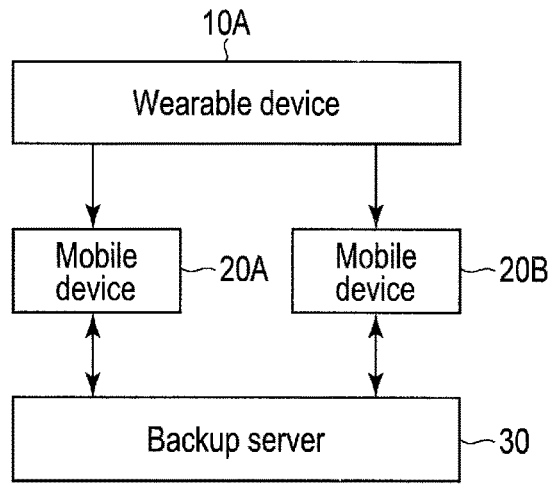
F I G. 9
| User ID | Mobile device ID | Last synchronization time information |
|---|---|---|
| User ID 1 | Mobile device ID 1 | Last synchronization time information 1 |
| | Mobile device ID 2 | Last synchronization time information 2 |
F I G. 10
| User ID | Wearable device ID |
|---|---|
| User ID 1 | Wearable device ID 1 |
F I G. 11

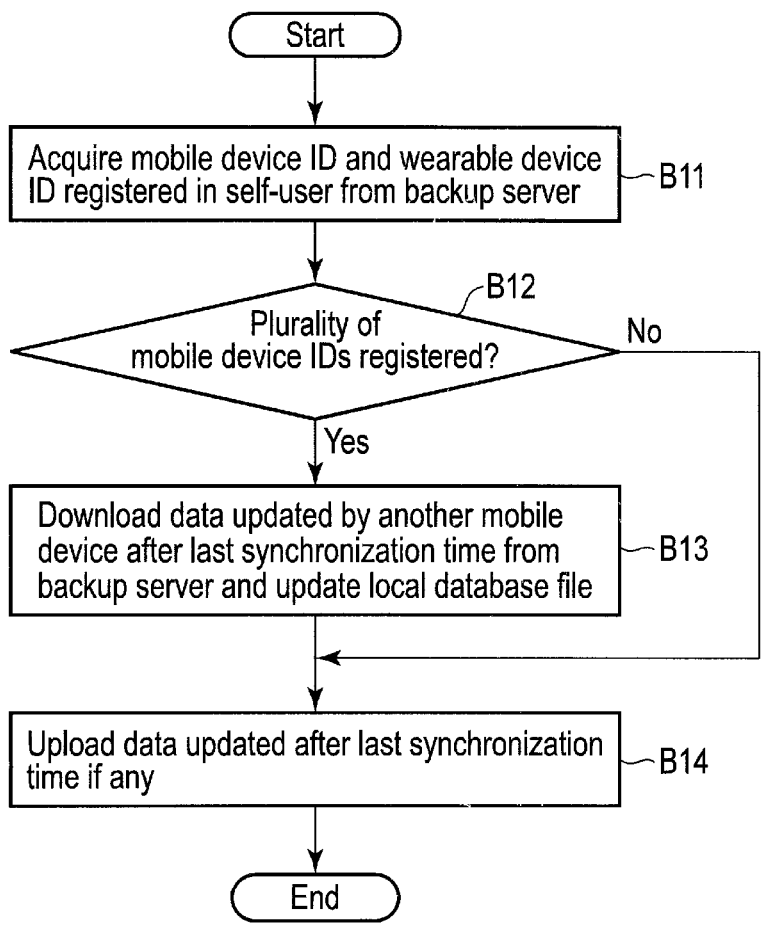
F I G. 12

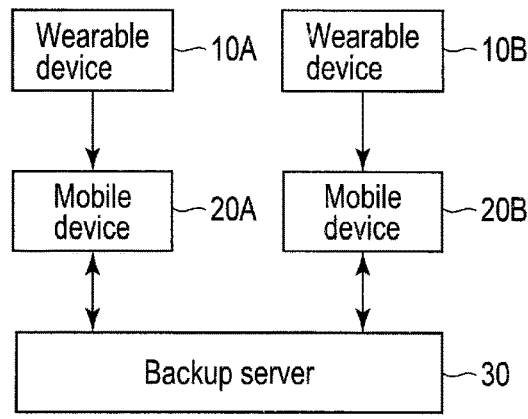
F I G. 13
| User ID | Wearable device ID |
|---|---|
| User ID 1 | Wearable device ID 1 |
| | Wearable device ID 2 |
F I G. 14
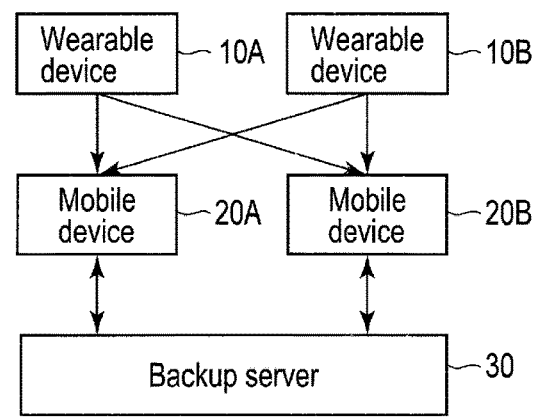
F I G. 15

| User ID | Mobile device ID | Last synchronization time information | Data item information |
|---|---|---|---|
| User ID 1 | Mobile device ID 1 | Last synchronization time information 1 | Data item information 1 |
| | Mobile device ID 2 | Last synchronization time information 2 | Data item information 2 |

F I G. 16

ELECTRONIC APPARATUS, SYSTEM AND SYNCHRONIZATION METHOD

CROSS-REFERENCE TO RELATED APPLICATIONS

This application is based upon and claims the benefit of priority from Japanese Patent Application No. 2014-184264, filed Sep. 10, 2014, the entire contents of which are incorporated herein by reference.

FIELD

Embodiments described herein relate generally to synchronization processing with a server comprising all data measured by an external device.

BACKGROUND

Recently, various mobile devices such as smartphones have been developed. These mobile devices comprise various functions, for example, a communication function and a position detection function.

Further, more recently, miniaturization of information equipment causes various wearable devices to be developed, and a market thereof is growing. A wearable device is an electronic apparatus which can be attached to a body of a user. The wearable device comprises a function of measuring, for example, number of steps, moving distance, calorie consumption, sleeping time, etc.

Some wearable devices do not comprise a display. Even if they comprise a display, the display may be small. Accordingly, data measured by the wearable devices is hard to confirm by the wearable devices.

To solve such a problem, data stored in a wearable device may be transferred to a mobile device by performing communication between the wearable device and the mobile device to confirm data measured by the wearable device using a display of the mobile device.

Since mobile devices which are portable devices may be lost or stolen, a service of backing up data accumulated in the mobile devices and measured by wearable devices in a backup server connected to a network has been considered.

Wearable devices are limited in size, and a large-capacity storage cannot be provided therein. Accordingly, after measured data is transmitted from a wearable device to a mobile device, the transmitted data is sometimes deleted from a storage of the wearable device.

At present, some users own a plurality of mobile devices. If, after measured data is transmitted from the wearable device (first wearable device) to a mobile device, measured data is transmitted from a wearable device to another mobile device (second mobile device), the data transmitted to the first mobile device cannot be confirmed in the second mobile device. Then, synchronization processing of data between the second mobile device and a backup server has been considered.

In the past, an effective synchronization method between a mobile device (electronic apparatus) and a backup server has not been considered.

BRIEF DESCRIPTION OF THE DRAWINGS

A general architecture that implements the various features of the embodiments will now be described with reference to the drawings. The drawings and the associated descriptions are provided to illustrate the embodiments and not to limit the scope of the invention.

FIG. 1 is an exemplary perspective view showing an example of an outer appearance of an external device according to an embodiment.

FIG. 2 shows a hardware configuration example of the external device shown in FIG. 1.

FIG. 3 shows an example of a hardware configuration example of an electronic apparatus according to the embodiment.

FIG. 4 is an exemplary functional block diagram showing an activity amount application.

FIG. 5 is an exemplary block diagram showing a configuration of a backup server.

FIG. 6 shows an example of a system in which one mobile device is registered for one wearable device.

FIG. 7 shows an example of a structure of a mobile device database file when one mobile device is associated with a user ID.

FIG. 8 is an exemplary block diagram showing a structure of a wearable device database file when one mobile device is associated with a user ID.

FIG. 9 shows an example of a system when one wearable device is registered in a plurality of mobile devices.

FIG. 10 shows an example of a structure of a mobile device database file when two mobile devices are associated with a user ID.

FIG. 11 is an exemplary block diagram showing a wearable database file when one wearable device is associated with a user ID.

FIG. 12 is an exemplary flowchart showing procedures of processing of a synchronization processor of a mobile device.

FIG. 13 is an exemplary block diagram showing a configuration of a backup system.

FIG. 14 shows a structure of a changed registration device database file.

FIG. 15 shows a configuration of a backup system comprising a plurality of wearable devices, a plurality of mobile devices and a backup server.

FIG. 16 shows a structure of a registration device database file when a plurality of wearable devices and a plurality of mobile devices are associated with each other.

DETAILED DESCRIPTION

Various embodiments will be described hereinafter with reference to the accompanying drawings.

In general, according to one embodiment, an electronic apparatus comprises a communication processor, a non-volatile storage device, a registration module, a transmission processor, and a reception processor. The communication processor acquires second data generated based on at least one first data item acquired by at least one sensor in a first external device by performing communication with the first external device. The registration module registers the acquired second data in a first file in the non-volatile storage device. The transmission processor transmits third data which is at least part of the first file to a server. The third data comprises data registered in the first file after the data is previously transmitted to the server. The server comprises a second file for registering all data transmitted from at least one second electronic apparatus, which corresponds to a user, comprising the electronic apparatus. The server registers the third data in the second file. The server comprises first electronic apparatus information indicative of the at least one second electronic apparatus. The reception processor receives fourth data not stored in the first file in the second file from the server, and registers the fourth data transmitted from the server in the first file. The reception processor does not receive the fourth data from the server when only the electronic apparatus corresponds to the user. The reception processor receives the fourth data from the server when the electronic apparatus and a third electronic apparatus different from the electronic apparatus of the at least one second electronic apparatus correspond to the user.

FIG. 1 is a perspective view showing an outer appearance of an external device. The external device is realized as a wearable device 10 which can be attached to a body of a user (for example, arm, neck, head, etc.). As the wearable device 10, a bracelet-type wearable device, a wristwatch-type wearable device, an eyeglasses-type wearable device, a headphone-type wearable device, etc., can be used. Suppose, hereinafter, the wearable device 10 is the bracelet-type wearable device.

The wearable device 10 comprises a belt 12 and a main body 13 attached to the belt 12.

The wearable device 10 is worn at a wrist of a user. The wearable device 10 is a so-called wristband. The wearable device 10 comprises at least one sensor. For example, the wearable device 10 comprises an acceleration sensor. The wearable device 10 has a function of measuring number of steps, moving distance, calorie consumption, sleeping time, etc., in accordance with a measured value of an acceleration sensor.

FIG. 2 shows a hardware configuration example of the wearable device 10.

The wearable device 10 comprises a controller 401, a main memory 402, a non-volatile memory 403, a short-range wireless communication module 404, an embedded controller (EC) 407, etc.

The controller 401 may be realized by a system-on-a-chip (SOC) comprising various functional modules comprising a CPU 401A. The CPU 401A functions as a processor (at least one core) configured to execute various programs loaded from the non-volatile memory 403 into the main memory 402.

These programs comprise an operation system and various applications/utility programs. The applications/utility programs comprise a wearable application.

The wearable application estimates the action of a user by use of at least one sensor 201. In this case, the wearable application may estimate which of being at rest, walking, being in motion by vehicle, and sleeping the current action of the user corresponds to. Whether the current action of the user is being at rest, walking, or being in vehicular motion may be estimated in accordance with a pattern of change of detected acceleration, etc. If it is estimated that the action is walking, a sensor data processor may measure the number of steps. The estimation of whether the current action of the user is sleeping or not may be made by estimating the posture of a user, for example, by an acceleration sensor. The current action of the user may be estimated to be sleeping on the condition that the estimated posture of the user is a specific posture, and the specific posture continues for a threshold time or more. Alternatively, whether it is sleeping or not may be estimated based on a detected value of a pulse wave sensor. If it is estimated to be sleeping, the sensor data processor may measure sleeping time.

A measured time is associated with data measured by the wearable application, and the data is accumulated in the non-volatile memory 403. When communication can be performed between the short-range wireless communication module 404 and a short-range wireless communication module of a mobile device, the wearable application transmits the accumulated data to the mobile device. When the accumulated data is normally transmitted, the wearable application erases the transmitted data from the non-volatile memory 403. The mobile device has a function of displaying a graph, etc., based on the transmitted data. Further, the mobile device has a function of storing the transmitted data. Further, the mobile device has a function of backing up the stored data in a server.

FIG. 3 shows a hardware configuration example of an electronic apparatus. The electronic apparatus can be realized as a portable terminal, for example, a tablet computer, a laptop or notebook computer or a PDA. Suppose, hereinafter, the electronic apparatus is realized as a tablet computer (hereinafter referred to as a mobile device 20).

The mobile device 20 comprises a CPU 301, a system controller 302, a main memory 303, a non-volatile memory 304, an audio codec 305, a short-range wireless communication module 306, a wireless LAN controller 307, a Bluetooth (registered trademark) (BT) controller 308, a GPS controller 309, an embedded controller (EC) 310, etc.

The CPU 301 is a processor configured to execute various programs loaded from the non-volatile memory 304 into the main memory 303. Examples of the various programs comprise an operation system (OS) 101 and various application programs. The various application programs comprise an activity amount application program 102.

The CPU 301 has a graphics processing unit (GPU) built-in. The graphics processing unit (GPU) is configured to control an LCD 24A in a display (touchscreen display) 24. A display signal generated by the GPU is sent to the LCD 24A. The LCD 24A displays a screen image based on the display signal. A touchpanel 24B is arranged on the upper side of the LCD 24A. The touchpanel 24B is a capacitive pointing device for performing input on a screen of the LCD 24A. A contact position of a finger on a screen, motion of the contact position, etc., are detected by the touchpanel 24B.

The system controller 302 connects between the CPU 301 and each component. The short-range wireless communication module 306 is configured to execute short-range wireless communication. The wireless LAN controller 307 is configured to execute wireless communication based on the IEEE 802.11 standard. The BT controller 308 executes short-range wireless communication conforming to the Bluetooth (registered trademark) standard. The GPS controller 309 calculates position information indicating a position/place of the mobile device 20 based on a signal received from a GPS satellite. The EC 310 has a function of powering on or off the mobile device 20.

FIG. 4 is a functional block diagram of the activity amount application program 102.

The activity amount application program 102 comprises a wearable device communication processor 501, a database file registration module 502, an acquisition processor 503, a synchronization processor 504, etc.

The wearable device communication processor 501 acquires activity amount information from the wearable device 10 by performing communication with the wearable device 10 through the short-range wireless communication module 306.

The database file registration module 502 registers data based on the activity amount information in an activity amount database file 511 in the non-volatile memory 304.

User ID information 512 indicating a user ID is stored in the non-volatile memory 304. A unique user ID is assigned to a user.

The acquisition processor 503 requests a backup server 30 to transmit a mobile device ID and a wearable device ID which are associated with a user ID indicated by the user ID information 512. The acquisition processor 503 performs the processing of acquiring the mobile device ID and wearable device ID transmitted from the backup server 30 upon request.

The synchronization processor 504 performs the processing of synchronizing a backup database file 602A in the backup server 30 and the activity amount database file 511 in the mobile device 20. The synchronization processor 504 comprises a transmission processor 504A, a reception processor 504B, etc. The backup server 30 comprises a storage (for example, hard disk drive or solid-state drive) storing the backup database file 602A in which data corresponding to all activity amount information generated by the wearable device 10 is registered.

The transmission processor 504A performs the processing of transmitting data newly registered in the activity amount database file 511 to the backup server 30. The backup server 30 performs the processing of registering data transmitted from the mobile device 20 in the backup database file 602A.

The reception processor 504B requests the backup server 30 to transmit data in the backup database file 602A registered, updated or deleted after a last synchronization date and time to receive data in the backup database file 602A not stored in the activity amount database file 511. The reception processor 504B performs the processing of receiving, from a backup server, the data in the backup database file 602A which is transmitted from the backup server 30 upon request and is registered, updated or deleted after the last synchronization date and time, and registering the received data in the activity amount database file 511.

The reception processor 504B performs the processing of transmitting the data in the activity amount database file 511 registered, updated or deleted after the last synchronization date and time to the backup server 30.

If a plurality of mobile device IDs are received, the reception processor 504B requests the backup server 30 to transmit the data in the backup database file 602A registered, updated or deleted after the last synchronization date and time. If a plurality of mobile device IDs are not received, in other words, only one mobile device ID is received, the reception processor 504B does not request the backup server 30 to transmit the data in the backup database file 602A registered, updated or deleted after the last synchronization date and time.

FIG. 5 is a block diagram showing a configuration of a backup server.

The backup server 30 comprises a communication processor 601, a storage device 602, an activity amount database management module 603, a mobile device database management module 604, a wearable device database management module 605, a synchronization processor 606, etc.

The communication processor 601 performs communication with the mobile device 20. The communication processor 601 acquires activity amount data in communication with the mobile device 20. The backup database file 602A, a mobile device database file 602B and a wearable device database file 602C are stored in the storage device (storage) 602. The activity amount database management module 603 manages the backup database file 602A. The mobile device database management module 604 manages the mobile device database file 602B. A mobile device ID corresponding to the mobile device 20 in the mobile device database file 602B is associated with a user ID corresponding to a user. That is, the association indicates a mobile device corresponding to a user. Registration of the association between the mobile device ID and the user ID in the mobile device database file 602B is performed by an operation of a user. Last synchronization date and time information indicating a date and time when synchronization is last performed is associated with the mobile device ID. That is, the association indicates a correspondence relationship between the mobile device and the last synchronization date and time. The wearable device database management module 605 manages the wearable device database file 602C. A wearable device ID corresponding to the wearable device 10 in the wearable device database file 602C is associated with the user ID corresponding to a user. That is, the association indicates a wearable device corresponding to a user. Registration of the association between the user ID and the wearable ID in the wearable device database file 602C is performed by an operation of a user. The synchronization processor 606 performs the processing of synchronizing the activity amount database file 511 with the backup database file 602A. If transmission of the data in the backup database file 602A registered, updated or deleted after the last synchronization date and time is requested from the mobile device 20, the synchronization processor 606 transmits the data in the backup database file 602A registered, updated or deleted after the last synchronization date and time to the mobile device 20.

Data in which a user ID corresponding to a user and a mobile device ID corresponding to the mobile device 20 are associated with each other is stored in the mobile device database file 602B. The association indicates a mobile device corresponding to a user. Further, the last synchronization date and time information indicating the last synchronization date and time can be associated with the mobile device ID.

Next, synchronization processing will be described.

[One Wearable Device and One Mobile Device]

As shown in FIG. 6, synchronization processing when one mobile device 20A is registered for one wearable device 10A will be described.

FIG. 7 shows an example of a structure of the mobile device database file 602B when one mobile device 20A is associated with a user ID.

As shown in FIG. 7, mobile device ID 1 is associated with user ID 1. Last synchronization date and time information 1 is associated with mobile device ID 1. Last synchronization date and time information 1 indicates a date and time when mobile device 20A corresponding to mobile device ID 1 last performed synchronization processing.

FIG. 8 shows an example of a structure of the wearable device database file 602C when a wearable device ID corresponding to one wearable device 10A is associated with a user ID.

As shown in FIG. 8, wearable device ID 1 is associated with user ID 1.

The backup server 30 transmits the mobile device ID and wearable device ID associated with the user ID to mobile device 20A at the request from the acquisition processor 503 of mobile device 20A. The reception processor 504B of mobile device 20A determines whether a mobile device ID different from mobile device ID 1 is received with reference to the mobile device ID transmitted from the backup server 30. In other words, it determines whether a plurality of mobile device IDs are received. Since a device different from mobile device ID 1 is not associated with user ID 1 in the mobile device database file 602B, the reception processor 504B does not request the backup server 30 to transmit the data in the backup database file 602A registered, updated or deleted after the last synchronization date and time. As a result, the reception processor 504B of mobile device 20A does not receive the data in the backup database file 602A registered, updated or deleted after the last synchronization date and time.

The reception processor 504B requests the backup server 30 to transmit data in a backup data corresponding to a user ID, and synchronization processing is performed between the synchronization processor 504 and the backup server 30, if the activity amount database file 511 of the mobile device 20 is broken, or if all data is retaken from the backup server 30 at the date and time of, for example, reinstalling an application.

[One Wearable Device and Plurality of Mobile Devices]

FIG. 9 shows a system when one wearable device is registered in a plurality of mobile devices.

As shown in FIG. 9, one wearable device 10A can perform communication with a plurality of mobile devices 20A and 20B.

FIG. 10 shows an example of a structure of the mobile device database file 602B when a mobile device ID corresponding to two mobile devices 20A and 20B is associated with a user ID.

As shown in FIG. 10, mobile device ID 1 and mobile device ID 2 are associated with user ID 1. Last synchronization date and time information 1 is associated with mobile device ID 1. Last synchronization date and time information 2 is associated with mobile device ID 2.

Last synchronization date and time information 1 indicates the date and time when mobile device 20A corresponding to mobile device ID 1 last performed synchronization processing. Last synchronization date and time information 2 indicates a date and time when mobile device 20B corresponding to mobile device ID 2 last performed synchronization processing.

FIG. 11 shows an example of a structure of the wearable device database file 602C when a wearable device ID corresponding to one wearable device 10A is associated with a user ID.

As shown in FIG. 11, wearable device ID 1 is associated with user ID 1.

The backup server 30 transmits all mobile device IDs associated with a user ID to mobile device 20A at the request from, for example, the acquisition processor 503 of mobile device 20A. The reception processor 504B of mobile device 20A determines whether a device different from mobile device ID 1 is associated with user ID 1 with reference to a mobile device ID transmitted from the backup server 30. In other words, the reception processor 504B of mobile device 20A determines whether a plurality of mobile device IDs are associated with user ID 1. Since a mobile device ID (mobile device ID 2) different from mobile device ID 1 is associated with user ID 1 in the mobile device database file 602B, the reception processor 504B requests the backup server 30 to transmit the data in the backup database file 602A registered, updated or deleted by another mobile device after the last synchronization date and time of mobile device 20A.

The synchronization processor 606 transmits only the data in the backup database file 602A registered, updated or deleted after the last synchronization date and time of mobile device 20A to mobile device 20A based on last synchronization date and time information 1. The reception processor 504B of mobile device 20A registers the transmitted data in the activity amount database file 511.

When synchronization processing is performed, the transmission processor 504A deletes data from a wearable device corresponding to a wearable device ID associated with other mobile device IDs from the non-volatile memory 304, and does not upload it in the backup server 30.

If update of the activity amount database file 511 (transmission of the data in the backup database file 602A registered, updated or deleted by another mobile device after the last synchronization date and time) is not requested for a fixed period of time in a system shown in FIG. 9 when the backup server 30 is downloaded from a specific mobile device, the mobile device database management module 604 inquires of the specific mobile device whether a mobile device ID corresponding to the specific mobile device can be deleted from the mobile device database file 602B. If it is indicated that the mobile device ID can be deleted from the specific mobile device, the mobile device database management module 604 deletes the mobile device ID corresponding to the specific mobile device associated with a user ID from the mobile device database file 602B. Data traffic between the mobile device 20 and the backup server 30 can be reduced by reducing update confirmation of the activity amount database file 511 by the deletion.

FIG. 12 is a flowchart showing procedures of the processing of the synchronization processor 504 of mobile device 20A.

The acquisition processor 503 requests the backup server 30 to transmit a mobile device ID and a wearable device ID which are registered in a user ID of a self-user (and which correspond to a user) (step B11). The reception processor 504B determines whether a plurality of mobile device IDs are registered for the user ID (step B12). If it is determined that the plurality of mobile device IDs are registered in the user ID (Yes in step B12), the reception processor 504B requests the backup server 30 to transmit the data in the backup database file 602A registered, updated or deleted by another mobile device after the last synchronization date and time of mobile device 20A (step B13). The backup server 30 transmits the data in the backup database file 602A registered, updated or deleted after the date and time indicated by last synchronization date and time information 1 to mobile device 20A based on last synchronization date and time information 1 associated with mobile device ID 1. The reception processor 504B of mobile device 20A receives data transmitted from the backup server 30 upon request. The reception processor 504B of mobile device 20A updates the activity amount database file 511 based on the received data (step B13).

If it is determined that the plurality of mobile device IDs are not registered in the user ID (No in step B12), the reception processor 504B of mobile device 20A need not receive data from the backup server 30; thus, it does not request the backup server 30 to transmit the data in the backup database file 602A registered, updated or deleted by another mobile device after the last synchronization date and time of mobile device 20A. Thus, the reception processor 504B of mobile device 20A does not receive the data in the backup database file 602A registered, updated or deleted by another mobile device after the last synchronization date and time of mobile device 20A.

If it is determined that the plurality of mobile device IDs are not registered in the user ID (No in step B12) or after step B13 is executed (after reception processing is terminated), the transmission processor 504A determines whether data in the activity amount database file 511 registered, updated or deleted after the last synchronization date and time is present. If the data registered, updated or deleted after the last synchronization date and time is present, the transmission processor 504A transmits the data in the activity amount database file 511 registered, updated or deleted after the last synchronization date and time to the backup server 30 (step B14).

[Plurality of Wearable Devices and Plurality of Mobile Devices]

A case where a new wearable device is registered for a system configuration shown in FIG. 9 will be described.

FIG. 13 shows a configuration of a backup system comprising wearable devices 10A and 10B, mobile devices 20A and 20B, the backup server 30, etc. FIG. 13 is a block diagram showing the configuration of the backup system after the mobile device database file 602A is changed.

In FIG. 13, the backup system comprises wearable devices 10A and 10B and mobile devices 20A and 20B. Wearable device 10A is registered in mobile device 20A. Mobile devices 20A and 20B are already registered in the mobile device database file 602B. Wearable device 10B is not registered in the wearable device database file 602C.

Registration of new wearable device 10B is requested from mobile device 20A or mobile device 20B. The wearable device database management module 605 inquiries of the mobile device which made the request whether the registration is made in either mobile device 20A or mobile device 20B for new wearable device 10B. Mobile device 20A displays in the LCD 24A a screen for inquiring of a user which of mobile device 20A and mobile device 20B is registered for a new wearable device.

If an operation for registering mobile device 20B in the new wearable device 10B is performed, the mobile device which made the request informs the backup server 30 that mobile device 20B is assigned to the new wearable device 10B.

The wearable device database management module 605 changes the wearable device database file 602C shown in FIG. 11. FIG. 14 shows a structure of the changed wearable device database file 602C.

Wearable device ID 1 and wearable device ID 2 are associated with user ID 1.

Further, mobile device ID 1 may be associated with wearable device ID 1. Further, mobile device ID 2 may be associated with wearable device ID 2.

[Plurality of Wearable Devices and Plurality of Mobile Devices]

FIG. 15 shows a configuration of a backup system comprising a plurality of wearable devices 10A and 10B, a plurality of mobile devices 20A and 20B and the backup server 30.

As shown in FIG. 15, the backup system comprises wearable devices 10A and 10B and mobile devices 20A and 20B. Wearable device 10A and wearable device 10B are registered in mobile devices 20A and 20B, respectively.

Data which can be acquired is different between wearable device 10A and wearable device 10B, or precision of data is different even if the same data is acquired.

Data item information 1 comprises a plurality of item IDs corresponding to respective data items measured by wearable device 10A. Data item information 2 comprises a plurality of item IDs corresponding to respective data items measured by wearable device 10B.

FIG. 16 shows a structure of the mobile device database file 602B when a plurality of wearable device IDs corresponding to a plurality of wearable devices and a plurality of mobile device IDs corresponding to a plurality of mobile devices are associated with a user ID.

Mobile device ID 1 and mobile device ID 2 are associated with user ID 1. Backup item information 1 is associated with mobile device ID 1. Backup item information 2 is associated with mobile device ID 2.

Backup item information 1 comprises an item ID corresponding to a data item for which synchronization processing is performed by mobile device 10A, of the data items measured by wearable device 10A and wearable device 10B. Backup item information 2 comprises an item ID corresponding to a data item for which synchronization processing is performed, of the data items measured by wearable device 10A and wearable device 10B. The data item to be backed up is designated by a user.

When the synchronization processing is performed, the synchronization processor 504 of the mobile device 20 indicates an item ID included in the selected backup item information to the synchronization processor 606 of the backup server 30. The synchronization processor 606 and the synchronization processor 504 perform synchronization processing of the data item according to the item ID indicated to the synchronization processor 606.

If a registration device database file indicating whether other electronic apparatuses which can transmit data acquired from a wearable device to a backup server are present indicates that there are no other electronic apparatuses which can transmit the data acquired from the wearable device to the backup server, a communication fee of data transmitted between the mobile device and the backup server can be reduced by preventing the synchronization processing from being performed, and synchronization can be efficiently performed with the server.

In the above embodiment, the mobile device requests the backup server 30 to transmit the data in the backup database file 602A registered, updated or deleted after the last synchronization date and time; however, whether a plurality of mobile device IDs are associated with a user ID may be determined, and whether to transmit the data in the backup database file 602A registered, updated or deleted after the last synchronization date and time may be determined based on the determination result.

It should be noted that the above-mentioned various kinds of processing in the present embodiment can be reduced to a computer program, which makes it possible to easily realize the same effects as the present embodiment only to install the computer program in a computer through a computer readable storage medium storing the computer program and to execute the installed computer program.

The various modules of the systems described herein can be implemented as software applications, hardware and/or software modules, or components on one or more computers, such as servers. While the various modules are illustrated separately, they may share some or all of the same underlying logic or code.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An electronic apparatus assigned with a first apparatus identifier, the electronic apparatus being able to be connected to a wearable sensing device, the electronic apparatus comprising:
  a non-volatile storage device comprising a data file that stores data sensed by the wearable sensing device; and
  a processor that communicates with a server while performing synchronization of a backup file stored in the server and the data file, the server comprising a storage that stores the backup file of a first data file stored in the non-volatile storage device in the electronic apparatus and of a second data file stored in a second electronic apparatus assigned with a second apparatus identifier, a user identifier being assigned to at least one of the electronic apparatus or the second electronic apparatus, and the storage stores an apparatus file storing correspondence between the user identifier and at least one of the first apparatus identifier or the second apparatus identifier, wherein
  the processor requests the server to transmit the at least one of the first apparatus identifier or the second apparatus identifier corresponding to the user identifier of a user of the wearable sensing device,
  when the processor receives the first apparatus identifier and the second apparatus identifier corresponding to the user identifier, the processor synchronizes the data file stored in the non-volatile storage device and the backup file stored in the storage of the server by:
    requesting the server transmit update data stored in the backup file which was updated by the second electronic apparatus after a last synchronization by the electronic apparatus,
    receiving the update data transmitted from the server, and
    updating the data file in the non-volatile storage device based on the update data.

2. The electronic apparatus of claim 1, wherein when the processor receives the first apparatus identifier and does not receive the second apparatus identifier, the processor does not request the server to transmit the update data.

3. The electronic apparatus of claim 2, wherein when the processor receives the first apparatus identifier and does not receive the second apparatus identifier, the processor transmits third data which was updated by the processor after the last synchronization.

4. The electronic apparatus of claim 1, wherein the apparatus file further stores correspondence between the first apparatus identifier and last synchronization time information of the first electronic apparatus and correspondence between the second apparatus identifier and last synchronization time information of the second first electronic apparatus.

5. The electronic apparatus of claim 4, wherein the server is configured to transmit the update data to the first electronic apparatus based on the last synchronization time information of the second electronic apparatus.

6. The electronic apparatus of claim 1, wherein the data sensed by the wearable sensing device comprises data indicative of action of the user or data indicative of activity amount of the user.

7. A system comprising:
  a first electronic apparatus assigned with a first apparatus identifier;
  a second electronic apparatus assigned with a second apparatus identifier; and
  a server, wherein
  a user identifier is assigned to at least one of the first electronic apparatus or the second electronic apparatus,
  each of the first electronic apparatus and the second electronic apparatus is able to be connected to a wearable sensing device,
  each of the first electronic apparatus and the second electronic apparatus comprises:
    a non-volatile storage device comprising a data file that stores data sensed by the wearable sensing device; and
    a processor that communicates with the server while performing synchronization of a backup file stored in the server and the data file, the server comprises:
    a storage that stores the backup file of a first data file stored in the non-volatile storage device in the first electronic apparatus and of a second data file stored in the non-volatile storage device in the second electronic apparatus and an apparatus file that stores correspondence between the user identifier and at least one of the first apparatus identifier or the second apparatus identifier,
  the processor of the first electronic apparatus requests the server to transmit the at least one of the first apparatus identifier or the second apparatus identifier corresponding to the user identifier of a user of the wearable sensing device,
  the server transmits the at least one of the first apparatus identifier or the second apparatus identifier corresponding to the user identifier to the first electronic apparatus,
  when the processor of the first electronic apparatus receives the first apparatus identifier and the second apparatus identifier corresponding to the user identifier, the processor of the first electronic apparatus synchronizes the data file stored in the non-volatile storage device and the backup file stored in the storage of the server by:
  requesting the server transmit update data stored in the backup file which was updated by the second electronic apparatus after a last synchronization by the first electronic apparatus,
  receiving the update data from the server, and
  updating the data file in the non-volatile storage device of the first electronic apparatus based on the update data.

8. The system of claim 7, wherein when the processor of the first electronic apparatus receives the first apparatus identifier and does not receive the second apparatus identifier, the processor of the first electronic apparatus does not request the server to transmit the update data.

9. The system of claim 8, wherein when the processor receives the first apparatus identifier and does not receive the second apparatus identifier, the processor is further configured to transmit third data which was updated by the processor after the last synchronization.

10. The system of claim 7, wherein the apparatus file stores correspondence between the first apparatus identifier and last synchronization time information of the first electronic apparatus and correspondence between the second apparatus identifier and last synchronization time information of the second first electronic apparatus.

11. The system of claim 10, wherein the server transmits the update data to the first electronic apparatus based on the last synchronization time information of the second electronic apparatus.

12. The system of claim 7, wherein the data sensed by the wearable sensing device comprises data indicative of action of the user or data indicative of activity amount of the user.

13. A synchronization method of a system comprising:
a first electronic apparatus assigned with a first apparatus identifier;
a second electronic apparatus assigned with a second apparatus identifier, a user identifier being assigned to the first electronic apparatus and the second electronic apparatus; and
a server, wherein
a user identifier is assigned to at least one of the first electronic apparatus or the second electronic apparatus,
each of the first electronic apparatus and the second electronic apparatus is able to be connected to a wearable sensing device,
each of the first electronic apparatus and the second electronic apparatus comprises:
  a non-volatile storage device comprising a data file that stores data sensed by the wearable sensing device; and
  a processor that communicates with the server while performing synchronization of a backup file stored in the server and the data file, and the server comprises:
  a storage that stores the backup file of a first data file stored in the non-volatile storage device in the first electronic apparatus and of a second data file stored in the non-volatile storage device in the second electronic apparatus and an apparatus file that stores correspondence between the user identifier and at least one of the first apparatus identifier or the second apparatus identifier, the method comprising:
requesting, by the processor of the first electronic apparatus, the server to transmit the at least one of the first apparatus identifier or the second apparatus identifier corresponding to the user identifier of a user of the wearable sensing device;
transmitting, by the server, the at least one of the first apparatus identifier or the second apparatus identifier corresponding to the user identifier to the first electronic apparatus;
when the processor of the first electronic apparatus receives the first apparatus identifier and the second apparatus identifier corresponding to the user identifier, the processor of the first electronic apparatus synchronizes the data file stored in the non-volatile storage device and the backup file stored in the storage of the server by:
  requesting the server to transmit update data stored in the backup file which was updated by the second electronic apparatus after a last synchronization by the first electronic apparatus;
  receiving the update data from the server, and
  updating the data file in the non-volatile storage device of the first electronic apparatus based on the update data.

14. The method of claim 13, wherein when the processor receives the first apparatus identifier and does not receive the second apparatus identifier, the processor does is configured not request the server to transmit the update data apparatus identifier corresponding to the user identifier.

15. The method of claim 14, wherein when the processor receives the first apparatus identifier and does not receive the second apparatus identifier, the processor is further configured to transmit third data which was updated by the processor after the last synchronization.

16. The method of claim 13, wherein the apparatus file further stores correspondence between the first apparatus identifier and last synchronization time information of the first electronic apparatus and correspondence between the second apparatus identifier and last synchronization time information of the second first electronic apparatus.

17. The method of claim 16, wherein the server is configured to transmit the update data to the first electronic apparatus based on the last synchronization time information of the second electronic apparatus.

18. The method of claim 13, wherein the data sensed by the wearable sensing device comprises data indicative of action of the user or data indicative of activity amount of the user.

* * * * *